United States Patent [19]

Klein et al.

[11] 4,387,107
[45] Jun. 7, 1983

[54] STABLE BENZOYL PEROXIDE COMPOSITION

[75] Inventors: Robert W. Klein, Blue Bell, Pa.; Mary E. Foxx, Plainsboro, N.J.

[73] Assignee: Dermik Laboratories, Inc., Fort Washington, Pa.

[21] Appl. No.: 216,972

[22] Filed: Dec. 16, 1980

Related U.S. Application Data

[63] Continuation-in-part of Ser. No. 60,392, Jul. 25, 1979, abandoned.

[51] Int. Cl.³ .......................................... A61K 31/075
[52] U.S. Cl. .................................................. 424/338
[58] Field of Search ......................................... 424/338

[56] References Cited

U.S. PATENT DOCUMENTS 3,535,422 10/1970 Cox et al. ............................ 424/164
4,056,611 11/1977 Young .................................... 424/62
4,075,353 2/1978 Mandy et al. ....................... 424/338

OTHER PUBLICATIONS

Merck Index, 9th Ed., 1976, Item 3288.
Handbook of Non-Prescription Drugs, pp. 317–323, 5th ed. 1977.

*Primary Examiner*—Leonard Schenkman
*Attorney, Agent, or Firm*—James A. Nicholson; Austin R. Miller; John Lezdey

[57] ABSTRACT

Aqueous benzoyl compositions peroxide stabilized with dioctyl sodium sulfosuccinate for treating mammals.

2 Claims, No Drawings

STABLE BENZOYL PEROXIDE COMPOSITION

This application is a continuation-in-part application of application Ser. No. 060,392, filed July 25, 1979 now abandoned.

FIELD OF THE INVENTION

This invention relates to aqueous compositions which contain benzoyl peroxide that are stabilized with dioctyl sodium sulfosuccinate that are utilized in the treatment of mammals.

PRIOR ART

Acne and sebhorrea are conditions of the human skin characterized by an excessive flow of sebum or skin oil, from the sebaceous glands which are located in the pilosebaceous apparatus. The channel through which sebum reaches the skin surface is the duct of the hair follicle. The presence of excess amounts of sebum in the duct and on the skin acts to block or stagnate the continuous flow of sebum from the follicle duct, thus producing a thickening of sebum which becomes a solid plug known as a comedone. When this occurs, hyperkeratinization of the follicular opening is stimulated, thus completely closing the duct. The usual result is a papule, pustule or a cyst, which are often contaminated with bacteria that cause secondary infections. These occurences characterize the disease today known as acne, and in lesser severity, sebhorrea.

Many topical therapeutical agents are employed in the treatment of acne and sebhorrea to prevent the blocking of the follicular ducts, to reopen the duct once it has become blocked, to act against the infecting bacteria or the thickened sebum, or to provide combinations of each of these actions. It is well known to use sulfur as a mild cutaneous irritant to remove the horny layer on the skin, and with it the debris clogging the follicular openings. Benzoyl peroxide compositions have been found to be effective in the treatment of acne, sebhorrea, and the associated secondary infections.

U.S. Pat. No. 3,535,422 discloses a therapeutic composition for the treatment of acne comprising a uniform dispersion of benzoyl peroxide in a fluid medium containing water and at least one organic emollient.

U.S. Pat. No. 4,056,611 discloses a therapeutic composition for the treatment of acne comprising a stable dispersion of finely divided particles of benzoyl peroxide in an aqueous alcohol vehicle having a single phase. The single phase of the composition is non-lipid and contains a non-ionic surface active agent that is soluble in the aqueous alcohol vehicle.

U.S. Pat. No. 4,075,353 discloses a process for treating skin infections caused by parasites, bacteria and/or fungal pathogens in animals by topically administering benzoyl peroxide to the afflicted animal.

The use of benzoyl peroxide and benzoyl peroxide compositions for the treatment of skin lesions is well detailed in the technical literature, as is the irritation caused by benzoyl peroxide. The effectiveness of benzoyl peroxide and typical problems associated with its use, such as excessive drying, heavy scaling, edema, burning, peeling, redness, excessive erythema, allergic contact dermatitis, and sensitization reactions, are discussed in the following references: Brogden, et al., Drugs, 8,417(1974); Poole, et al, Arch Derm. 102,400 (1972); Eaglstein, arch. Derm. 97,527 (1968); Pace, Can. Med. Ass. J. 93, 252(1965); Vasarinsh, Arch. Derm. 98,183(1968); Myslibroski, et al., AFP 15,86,(1977); Hare,Br.J. Clin.Prac. 29,63(1975); Fulton, et al., Arch. Derm 110,83(1974); and Wilkinson, et al., Can.Med-.Assn.J. 95,28(1966).

A reduction in, or control of, benzoyl peroxide irritations has been achieved by using certain gel formulations, or by temporarily suspending the topical application of the benzoyl peroxide compositions: Kuflik, et al., Curtis 17,175 (1976); Liddell,Br.J.Clin.Prac. 28,379(1974); and Kirton,Br. J.Clin.Prac. 21, 127(1967).

Prior art benzoyl peroxide compositions which contain merely finely divided benzoyl peroxide particles in an emulsion of water and certain select emollients provides the disadvantage that when the water content of the emulsion evaporates there remains most of the organic emollients and the large benzoyl peroxide particles on the surface of the skin near and in contact with the acne sites which may cause irritation.

Additionally, the use of large amounts of non-ionic surface active agents in such compositions, unless extremely fine particles of benzoyl peroxide are utilized, would cause a likelihood of irritation from the benzoyl peroxide.

Also, because of the powerful oxidizing properties of benzoyl peroxide, the inclusion of this substance in a conventional ointment or emulsion results in unstable compositions that soon display an unacceptable loss in keratolytic potency.

SUMMARY OF THE INVENTION

The present invention relates to novel therapeutic compositions containing benzoyl peroxide in an aqueous vehicle having greater stability and shelf life.

It has been surprisingly found that the use of dioctyl sodium sulfosuccinate in benzoyl peroxide formulations stabilize the composition and extends the shelf life of the active ingredients.

It has been further surprisingly found that in aqueous and hydroalcoholic vehicles the utilization of micronized benzoyl peroxide having a particle size of less than 150 microns in combination with dioctyl sodium sulfosuccinate as the surface active agent results in a composition which displays full stability with respect to the benzoyl peroxide component even when subjected to temperatures higher than those normally expected in the ordinary use of the product. Also, it has been found that the combination in an alcoholic aqueous gel, upon evaporation allows for a uniform release of the micronized benzoyl peroxide so as to obviate the burning and erythema experienced with other harsh gel formulations.

The aqueous and/or hydroalcoholic composition of the present invention contains from about 1 to about 30%, and preferably from about 5–15%, by weight, of benzoyl peroxide, preferably, having a particle size of less than about 150 microns with the mean average particle size being less than about 35 microns. Dioctyl sodium sulfosuccinate which serves as a surface active agent as well as providing for the increased stability of the composition is present in the amount of about 0.1 to about 10%, by weight, preferably about 0.1 to 4%, by weight of composition.

The use of hydroalcoholic gel formulations have been found to be especially advantageous since there is produced a stable composition which provides for a uniform distribution of the active ingredients.

DETAILED DESCRIPTION

The therapeutic compositions of the present invention must contain sufficient benzoyl peroxide to be therapeutically effective, and should not contain more peroxide than can be uniformly dispersed in the vehicle to form a smooth uniformly spreadable composition. Such considerations dictate that the composition contain least 1% and not more than 30% by weight of benzoyl peroxide, and preferably that the composition contain from about 5 to about 15%, by weight benzoyl peroxide. The benzoyl peroxide constituent of the composition should be high purity and preferably in the form of micronized finely divided crystalline particles having a mean average particle size of less than about 35 microns. The aqueous gel compositions of the present invention may also include a wetting agent such as the esters of sugars, long-chain alkyl phenols, long-chain mercaptans, long-chain amides, etc. in an amount of from 3 to 6%, by weight.

Another important component of the gel compositions of the present invention is the gelling agent. These may be selected both as to type and quantity to give products of various viscosities. In the preferred form of this invention, the gelling agent is selected so as to produce an elegantly formed and stable gel which is either semi-solid or pourable. A variety of gelling agents may be used for the present purposes. However, preferred gelling agents are pure microcrystalline cellulose, colloidal magnesium aluminum silicate, hydroxypropyl methyl cellulose and the so-called hydroxylated vinylic polymers, particularly, those disclosed in U.S. Pat. No. 2,798,053. Among those hydroxylated vinylic polymers of special interest herein are described generally as interpolymers of a monomeric monoolefinic acrylic acid, and from about 0.1 to about 10% by weight based on the total monomer of a monomeric polyether of an oligosaccharide in which the hydroxyl groups which are modified are esterfied with allyl groups with said polyether containing at least two allyl ether groups per oligosaccharide molecule. Commerically available interpolymers of this type are marketed under the trade name "Carbopol". These are described as being polymers of acrylic acid cross-lined with about 1% of a polyallyl ether of sucrose having an average of about 5.8 allyl groups for each sucrose molecule. These polymers have molecular weight in the order of magnitude of 1,000,000. Such polymers are available from the B. F. Goodrich Chemical Company and are sold under the trademark "Carbopol 934", "Carbopol 940" and "Carbopol 941".

The various Carbopols are distinguished from each other by the manufacture on the basis of their viscosity. The polymers are gelled by neutralizing them with an alkaline material. Suitable neutralizing agents are the organic amines among which may be mentioned triethanolamine, triethylamine, isopropylamine, diisopropylamine, etc. and inorganic bases, among which may be NaOH, KOH, Ca(OH)$_2$, etc.

The quantity of gelling agent that may be contained in the present compositions may also vary somewhat. Ordinarily, this will constitute about 0.3% to about 15% by weight, and preferably about 1% to about 5% by weight, based on the total weight of the finished composition.

The compositions of the present invention will also ordinarily contain substantial aqueous components. When water is present, it may also vary dependent on the nature of the product desired. Usually this will constitute between about 30–85%, based on the total weight of the finished product. It is also preferred to use demineralized water.

If an alcohol is employed to form the aqueous alcohol vehicles the alcohol must be soluble in water, serve as a cosolvent for the surface active agent in the vehicle and also serve as an antiseptic and drying aid when applied to the skin. Alkyl alcohols having from 1–6 carbon atoms meet the foregoing criteria and are used in the formulation of the competition of the invention. The compositions with from 10–80% by weight of one or more of these alcohols is sufficient to insure that the surface active agents will dissolve therein.

It is sometime advantageous to add additional therapeutically active ingredients to the present compositions which may serve to augment the activity of the benzoyl peroxide or to supplement them. A variety of materials may be used for this purpose. Of special interest as an auxiliary skin treating agent is the keratolytic agents and especially salicylic acid. When these are used, they may be employed over a range of concentrations which may vary from about 0.2% to about 8% by weight.

In the treatment of acne, the composition may also advantageously contain from 1–25% by weight of finely divided, micronized or colloidal sulfur. Sulfur is an antimicrobial and keralytic agent that has long been used in the treatment of acne. Although it is not known precisely how sulfur exerts its keratolytic effect on the skin, it is believed that the hydrogen sulfide, which if formed when sulfur is in contact with animal tissue, reacts with alkali in tissue fluids to produce active sulfides, which in turn, promote keratosis. The composition of sulfur with benzoyl peroxide produces significantly greater keratosis than either substance will when used alone.

If desired, minute amounts of a compatible acid base may be added to the composition to adjust the relative acidity or alkalinity thereof, the pH of the composition usually being adjusted to within the range 3.5 and 7.5, preferably about 5.0–6.0.

In addition, for purposes of formulating more elegant products, additional additives may be incorporated into the present composition. Typical among these may be emulsifying agents, emollients, preservatives, etc.

The gel composition of the present invention is applied topically to the skin of the patient by rubbing the gel in one or more times daily depending on the skin condition to provide drying, desquamative and antiseptic effects. Almost all persons who use the compositions of the present invention show a definite suppression of the acne erruption within the first few weeks of treatment. Moreover, the compositions of this invention have been demonstrated to be markedly more effective and faster acting than benzoyl peroxide containing emulsions or gel formulations of comparative strength previously known in the art.

The following examples are representative but not limited of therapeutic compositions prepared in accordance with the invention:

EXAMPLE I 495.0 mg. of purified water was mixed and 15.0 mg. of Carbopol 940 (a carboxy vinyl polymer, acid form, of B. F. Goodrich Co.) were added to the water while stirring. Stirring of the mixture was continued for 45 minutes. Then 4.095 mg. of sodium hydroxide in 4.91 ml. of purified water was added thereto as a partial neutralizing agent for the carbopol 940. Stirring of the mixture was continued for 10 minutes, whereupon 150.0 mg. of ethyl alcohol, 0.50 mg. of perfume and 0.50 mg. of methyl salicylate was added. To the stirred mixture was then added a mixture comprising 210.0 mg. of wet pack micronized benzoyl peroxide(50% benzoyl peroxide—50% water), 2.0 mg. of dioctyl sodium sulfosuccinate, and 81.0 mg. of purified water. The mixture was stirred for 30 more minutes until a smooth and elegant gel mixture was obtained.

The gel composition was suitable for use in this treatment of acne.

EXAMPLE II

Following the procedure of Example I the following composition was prepared:

| | |
|---|---|
| Benzoyl peroxide (micronized) | 5.46% by weight |
| Water | 46.69% by weight |
| Ethyl alcohol | 44.10% by weight |
| Colloidal magnesium aluminum silicate | 2.50% by weight |
| Hydroxypropylmethylcellulose | 1.00% by weight |
| Citric Acid | 0.05% by weight |
| Dioctyl sodium sulfosuccinate | 0.2% by weight |

EXAMPLE III

Following the procedure of Example I the following composition was prepared:

| | |
|---|---|
| Benzoyl peroxide (micronized) | 2.50% by weight |
| Water | 15.95% by weight |
| Ethyl alcohol | 70.00% by weight |
| Carboxy vinyl polymer (Carbopol 934) | 10.50% by weight |
| Hydroxypropylcellulose | 0.45% by weight |
| Dioctyl sodium sulfosuccinate | 0.20% by weight |

EXAMPLE IV

Following the procedure of Example I the following composition was prepared:

| | |
|---|---|
| Benzoyl peroxide (micronized) | 2.8% by weight |
| Water | 21.8% by weight |
| Ethyl alcohol | 70.0% by weight |
| Carboxy vinyl polymer (Carbopol 941) | 5.0% by weight |
| Potassium hydroxide | 0.2% by weight |
| Dioctyl sodium sulfosuccinate | 0.2% by weight. |

EXAMPLE V

Following the procedure of Example I the following composition was prepared:

| | |
|---|---|
| Benzoyl peroxide (micronized) | 15.00% by weight |
| Water | 54.85% by weight |
| Ethyl alcohol | 25.00% by weight |
| Colloidal magnesium aluminum silicate | 4.50% by weight |
| Sodium carboxymethylcellulose | 0.60% by weight |
| Citric acid | 0.05% by weight |
| Dioctyl sodium sulfosuccinate | 0.50% by weight |

EXAMPLE VI

Following the procedure of Example I the following composition was prepared:

| | |
|---|---|
| Benzoyl peroxide (micronized) | 5.00% by weight |
| Water | 81.47% by weight |
| Isopropyl alcohol | 10.00% by weight |
| Hydroxypropylmethylcellulose | 1.50% by weight |
| Xanthan gum | 0.03% by weight |
| Phosphoric acid | 0.03% by weight |
| Dioctyl sodium sulfosuccinate | 0.50% by weight |

EXAMPLE VII

Following the procedure of Example I the following composition was prepared:

| | |
|---|---|
| Benzoyl peroxide (micronized) | 8.00% by weight |
| Water | 73.74% by weight |
| Ethyl alcohol | 15.00% by weight |
| Hydroxypropylmethylcellulose | 1.50% by weight |
| Guar gum | 1.50% by weight |
| Tartaric acid | 0.06% by weight |
| Dioctyl sodium sulfosuccinate | 0.20% by weight. |

EXAMPLE VIII

Following the procedure of Example I the following composition was prepared:

| | |
|---|---|
| Benzoyl peroxide (micronized) | 15.00% by weight |
| Water | 57.53% by weight |
| Ethyl alcohol | 24.00% by weight |
| Microcrystalline cellulose | 2.50% by weight |
| Sodium carboxymethylcellulose | 0.50% by weight |
| Citric Acid | 0.07% by weight |
| Dioctyl sodium sulfosuccinate | 0.20% by weight |

EXAMPLE IX

Following the procedure of Example I the following composition was prepared:

| | |
|---|---|
| Benzoyl peroxide | 15.0% by weight |
| Water | 51.8% by weight |
| Isopropyl alcohol | 20.0% by weight |
| Sodium carboxymethylcellulose | 11.5% by weight |
| Sodium naphthalene sulfonic acid formaldehyde condensate | 1.0% by weight |
| Citric Acid | 0.2% by weight |
| Dioctyl sodium sulfosuccinate | 1.0% by weight |
| Sulfur (micronized) | 10.0% by weight |

EXAMPLE X

Following the procedure of Example I the following composition was prepared:

| | |
|---|---|
| Benzoyl peroxide | 7.50% by weight |
| Water | 65.75% by weight |
| Isopropyl alcohol | 15.00% by weight |
| Collodial magnesium aluminum silicate | 10.00% by weight |
| Polyethylene glycol polymer | 1.50% by weight |
| Citric Acid | 0.05% by weight |
| Dioctyl sodium sulfosuccinate | 0.20% by weight. |

EXAMPLE XI

Following the procedure of Example I the following composition was prepared:

| | |
|---|---|
| Benzoyl peroxide | 10.99% by weight |
| Water | 24.36% by weight |
| Ethyl alcohol | 50.10% by weight |
| Collodial magnesium aluminum silicate | 12.50% by weight |
| Hydroxypropylmethylcellulose | 1.00% by weight |
| Citric acid | 0.05% by weight |
| Dioctyl sodium sulfosuccinate | 1.00% by weight |

All of the compositions prepared in Example I to XI may be utilized topically on animals and humans in the treatment of skin disorders wherein benzoyl peroxide has been forthwith found to be effective.

EXAMPLE XII

A shampoo formulation comprising about 3.9% by weight of a 70% by weight benzoyl peroxide in water solution, about 50% by weight sodium lauryl sulfate(Sipon LS/B, shampoo base), about 6% by weight, doctyl sodium sulfosuccinate, about 2.5% by weight hydrated aluminum magnesium silicate, (Veegum K, R. T. Vanderbilt Co.), about 1.0% by weight methylcellulose (Methocel E, 417 Premium, Dow Chemical Co.), about 0.21% by weight citric acid, and about 35.6% by weight distilled water, is applied to a 1 year old dog(German Shepherd) afflicted with demodectic mange. After biweekly shampoo treatments over a period of approximately one month, the dog is in complete remission without deleterious side effects.

What is claimed is:

1. A therapeutic aqueous benzoyl peroxide gel composition comprising from about 2.5 to about 15% by weight of micronized benzoyl peroxide having a particle size of less than 150 microns with a mean average particle size in said composition of less than 35 microns and a stabilizing agent which comprises 0.1 to 4% by weight of dioctyl sodium sulfosuccinate.

2. A therapeutic aqueous alcoholic gel composition suitable for the treatment of acne comprising:
   a. about 5% by weight of micronized benzoyl peroxide having a particle size of less than 150 microns, and having a mean average particle size in said composition of less than 35 microns;
   b. about 0.2% by weight of dioctyl sodium sulfosuccinate;
   c. about 0.3% to about 3% by weight of a hydroxylated vinylic polymer gelling agent; and
   d. about 15% by weight of an alkanol and water.

* * * * *